United States Patent [19]

D'Andrea

[11] Patent Number: 5,520,646
[45] Date of Patent: May 28, 1996

[54] DIAGNOSTIC MARKING CATHETER SYSTEM FOR USE IN RADIATION DIAGNOSIS PROCEDURE

[76] Inventor: Mark A. D'Andrea, 528 Beechwood Dr., Tyler, Tex. 75701

[21] Appl. No.: 205,896

[22] Filed: Mar. 3, 1994

[51] Int. Cl.⁶ .......................... A61M 29/00; A61M 25/00
[52] U.S. Cl. ........................... 604/96; 604/101; 604/280; 606/193
[58] Field of Search ............................ 624/96–103, 263, 624/264, 280; 606/192, 193; 128/656, 658

[56] References Cited

U.S. PATENT DOCUMENTS

| | | | |
|---|---|---|---|
| 899,477 | 9/1908 | Williams | 606/193 |
| 3,173,418 | 3/1965 | Baran | 604/101 X |
| 3,435,826 | 4/1969 | Fogarty . | |
| 3,467,101 | 9/1969 | Fogarty et al. . | |
| 3,543,744 | 12/1970 | LePar . | |
| 3,841,304 | 10/1974 | Jones . | |
| 4,263,917 | 4/1981 | Moss . | |
| 4,318,410 | 3/1982 | Chin . | |
| 4,349,033 | 9/1982 | Eden | 604/96 X |
| 4,471,779 | 9/1984 | Antoshkiw et al. . | |
| 4,744,366 | 5/1988 | Jang | 604/101 X |
| 4,775,362 | 10/1988 | Kronner . | |
| 4,813,934 | 3/1989 | Engelson et al. . | |
| 4,919,651 | 4/1990 | Doane . | |
| 5,019,042 | 5/1991 | Sahota | 604/101 |
| 5,049,132 | 9/1991 | Shaffer et al. | 604/101 |
| 5,122,113 | 6/1992 | Hattler | 604/26 |
| 5,135,494 | 8/1992 | Engelson et al. . | |
| 5,147,300 | 9/1992 | Robinson et al. | 604/97 |
| 5,342,305 | 8/1994 | Shonk | 604/101 |

FOREIGN PATENT DOCUMENTS

| | | | |
|---|---|---|---|
| 699316 | 12/1964 | Canada | 606/193 |
| 1511557 | 5/1978 | United Kingdom | 604/101 |

*Primary Examiner*—John D. Yasko
*Assistant Examiner*—Adam J. Cermak
*Attorney, Agent, or Firm*—Lockwood, Alex, Fitzgibbon & Cummings

[57] ABSTRACT

The present invention provides a significantly improved diagnostic tool and procedure for radiation therapy in or near body cavities accessible through existing orifices. This invention makes use of a flexible catheter and balloon. The balloon is inflated by fluid communication through the catheter. This invention makes use of several preferable embodiments which provide radiopaque references, seals, control of movement, and drainage. The radiopaque references are provided by means of radiopaque lines painted on the balloon's interior or exterior surface, by means of the use of radiopaque fluid to inflate the balloon, or by means of a slidable clip made of radiopaque material which is positioned at the patient's orifice. Sealing is provided by means of the slidable clip which also permits adjustment of the balloon size and shape. Control of movement is achieved through the use of a small balloon usually located near the patient's orifice. Drainage, often required when performing this procedure in the bladder, is achieved by the use of a Foley-type catheter.

14 Claims, 1 Drawing Sheet

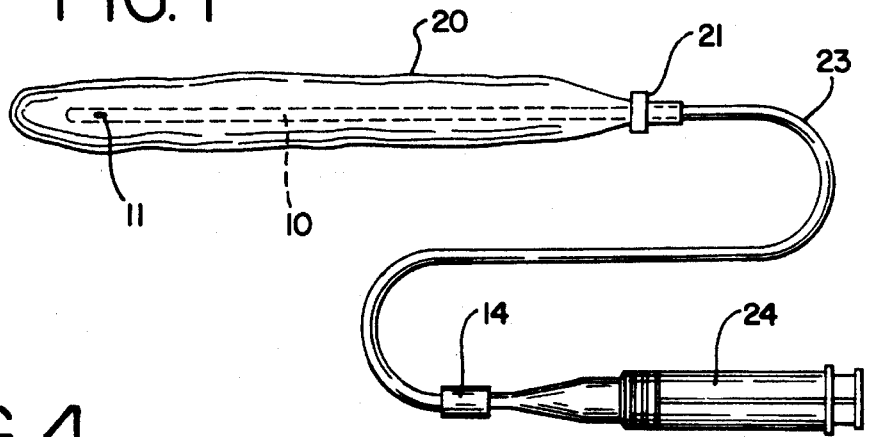
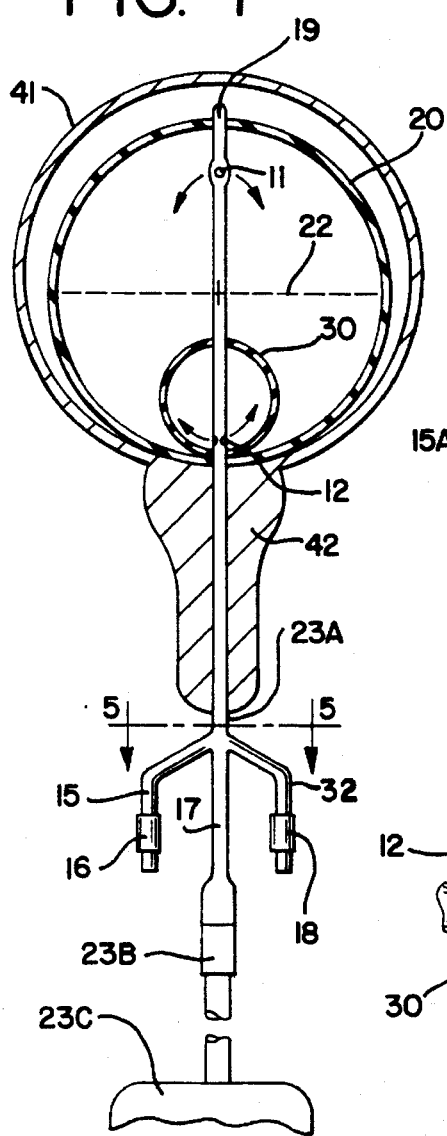
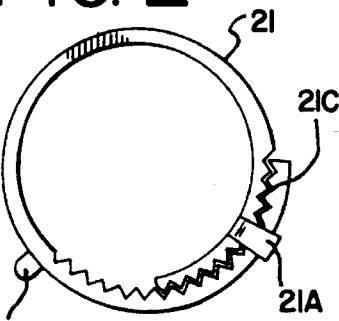
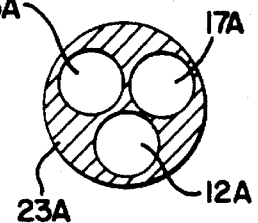
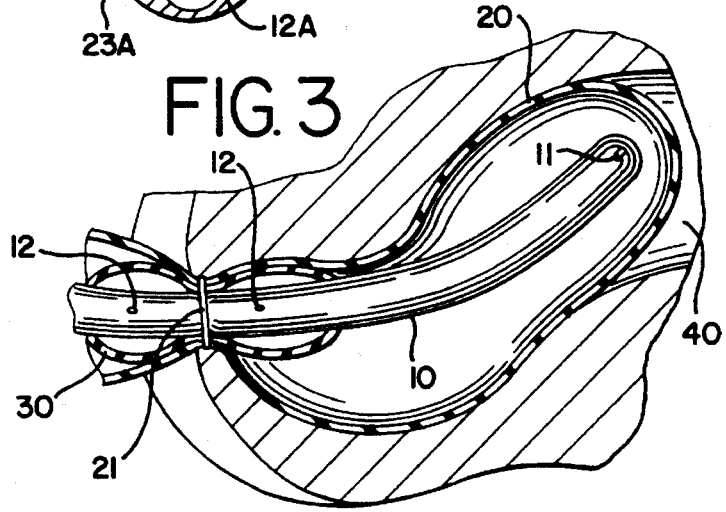

DIAGNOSTIC MARKING CATHETER SYSTEM FOR USE IN RADIATION DIAGNOSIS PROCEDURE

BACKGROUND OF THE INVENTION

The present invention generally relates to diagnostic procedures and devices used prior to radiation therapy. This invention generally consists of a catheter with a balloon attached to its distal end. It is intended to be inserted into living body cavities through existing body orifices. Once the catheter and its balloon are inserted in the prescribed manner into the body cavity, the balloon is inflated to mark the boundary of the body cavity during radiographic examination. The inflated balloon may also be used to move, push, or otherwise manipulate body tissue during the radiation therapy or diagnostic procedure.

Because the rectal, esophageal, bladder and other larger body cavities do not tend to branch off like blood vessels and do not require percutaneous insertion, this invention is fundamentally distinct from devices such as those use for angioplasty, angiography, and the like. This invention is generally unique in design for its intended applications.

This invention is intended to have a plurality of functions. It may be used to identify the boundary of a body cavity or otherwise provide reference to assist the physician in identifying the appropriate treatment area. It may also be used to manipulate a body cavity to assist the physician in identifying the appropriate treatment area or to push tissues out of the treatment area. The invention permits the introduction of air or of various diagnostic fluids free from risk that toxins or other contaminants could contact the patient. Also, the invention can be used in a variety of body cavities.

It is a general object of the present invention to provide a significantly improved diagnostic tool and procedure for radiation therapy in or near body cavities accessible through existing orifices.

Another object of this invention is to provide an improved apparatus and method to provide the physician with a view of the body cavity during radiographic viewing, such as X-ray radiography.

Another object of this invention is to enable the physician to move, push or otherwise manipulate body tissue for the purpose of improved diagnoses or therapy.

Another object of this invention is to enable introduction of radiographic fluids or air into the body cavity of the patient without subjecting the patient to risk from those radiographic fluids.

Another object of this invention is to permit the physician to tailor the size of the balloon to the particular diagnostic requirements of the body cavity through the use of a slidable clip or the like Another object of this invention is that the slidable clip, when included, may be made of a radiopaque material to enable radiographic marking of the opening into the body cavity.

Another object of this invention is to maintain the position of the diagnostic balloon through the use of a smaller balloon located within a larger, primary balloon.

Another object of the present invention is to provide a device and method suitable for use in the bladder by providing an elongated insertion catheter having drainage characteristics.

Another object of this invention is to provide an improved apparatus and method which allows the provision of radiopaque reference lines at desired locations within a variety of body cavities.

These and other objects and advantages of the present invention will be apparent from the following description.

SUMMARY OF THE INVENTION

This invention utilizes a catheter for insertion into a body cavity. A large or primary balloon is secured to a distal portion of a tubular catheter body, the balloon being positioned and sized for insertion into the particular type of body cavity. The proximal end of the catheter has one or a plurality of branches to enable fluid communication through various channels in the catheter body, depending upon the embodiment. These branches preferably utilize one-way or two-way valves, regulators, hypodermic syringes or the like for the introduction, control and withdrawal of the fluids into and out of the large balloon.

The fluid with which the balloon may be filled can be a biocompatible gas, such as air, or a biocompatible liquid, such as saline solution. In some embodiments, the balloon may have one or more radiopaque reference markings on its interior or exterior surface for the purpose of radiographic viewing. When the physician wishes to identify more clearly the boundary of a body cavity, the primary balloon is preferably filled with a radiopaque fluid such as a barium radiopaque composition. The balloon(s) of the catheter device may also be used to move, expand, or otherwise manipulate the body cavity by balloon inflation.

A secondary inner balloon which is substantially smaller than the primary large outer balloon can be included to assist in holding the device in place within the body cavity. This secondary balloon is located generally within and at the proximal end of the primary balloon. It will have a fluid communication system separate from the other fluid communication systems within the device. When inflated, the secondary balloon secures the catheter device within the body cavity, and it also can be used to mark the body orifice, particularly when filled with radiopaque fluid.

In the preferred embodiment, this invention uses a slidable clip with which the physician can adjust the longitudinal size of the primary balloon. The physician premeasures the desired length of the primary balloon material and the desired catheter penetration length and secures the slidable clip over the primary balloon which is, as manufactured, sealed onto and over the catheter body at a proximal seal location. This movement of the slidable clip in effect adjusts the expansion size of the primary balloon by providing a variable proximal sealing location which can be selected by the physician to precisely tailor the primary balloon to the particular body cavity being subjected to diagnosis. For example, the clip and thus the approximate proximal end of the primary balloon can be positioned at the body cavity orifice or opening. This slidable clip has the features of easy accessibility and positive manipulability by the physician, minimal patient trauma, and an approximately circular overall shape so as to fit closely over the catheter body and balloon(s).

One embodiment of this invention incorporates a Foley-type catheter for radiation diagnosis in the bladder. A Foley-type catheter can enable the necessary drainage of urine or the like during the diagnostic procedure.

BRIEF DESCRIPTION OF THE DRAWINGS

In the course of this description, reference will be made to the accompanying drawings, wherein:

FIG. 1 is an elevation view of an embodiment of the invention, including the primary or large balloon sealed to the catheter and also showing a fitting at its proximal end;

FIG. 2 is a plan view of an embodiment of a slidable adjustment clip, demonstrating its preferred characteristics;

FIG. 3 demonstrates an embodiment of the invention, shown principally in cross-section, in use within the rectum, shown in cross-section;

FIG. 4 demonstrates another embodiment of the invention, shown principally in cross-section, in use within a bladder, shown in cross-section; and FIG. 5 is a cross-sectional view along the line 5—5 of FIG. 4.

DESCRIPTION OF THE PREFERRED EMBODIMENTS

FIG. 1 shows a diagnostic catheter, generally designated as 10, having a body or tube member 23. A primary balloon 20, which is relatively large in relationship to the rest of the catheter and any other balloon(s) which may be included on the diagnostic catheter 10, is positioned over and sealed onto a distal end length or portion of the body member 23. This distal end length and its primary balloon 20 are intended to be inserted by the physician into the patient's body cavity during a diagnostic procedure.

The primary balloon 20 is typicality made of an elastomeric polymer material. Catheter 10 is typically made of a polymeric material, a metallic material, or a combination of polymeric material with metallic material, such as strands of metal imbedded in polymer in order to create the desired balance of flexibility and rigidity.

In this embodiment, the length and profile of the primary balloon is adjustable by means of an adjustment member or assembly. Illustrated in this regard in this embodiment is a slidable clip 21. Although the balloon is necessarily already sealed onto the body member 23 at its proximal end (as well as at its distal end in some embodiments), the adjustment member allows the physician to select a location for the proximal end of the primary balloon, such as by releasing the clip, manually moving it to the desired proximal end location of the balloon, and securing the clip at this desired location along the length of the primary balloon 20. In this manner, the balloon will inflate in the proximal direction only up until the location of this adjustment member 21.

At its proximal end, body member 23 of the catheter 10 may juncture into a plurality of branches (two in the embodiment of FIG. 3 and three in the embodiment of FIG. 4). Each such branch contains a separate, isolated fluid line which communicates through the catheter and to appropriate openings such as the illustrated holes 11, 12.

The primary balloon is inflated through one or more holes 11. Each hole 11 communicates through the catheter tube member 23 to fitting 14. Fitting 14 connects with a pressurized fluid source, which may be a biocompatible gas such as air or a biocompatible liquid such as saline solution. The fluid may also be radiopaque, if the physician determines that the diagnostic procedure requires its use. The means of pressurization may be a hypodermic syringe, such as that illustrated at 24. The means of pressurization may also be a pressurized tank, in-house line plumbed to the treatment room, or the like. If these latter pressurization sources are used, fitting 14 may include a valve or regulator.

Slidable clip 21 secures the large or primary balloon 20 onto the catheter by clamping down the balloon onto the catheter body at the location inside of the clip or clamp. The physician locates the clip so that the desired amount of balloon material and depth of catheter penetration are achieved. The physician manipulates the slidable clip with his or her hand(s) and, once in place and secured, is free to use both hands for other subsequent steps of the diagnostic procedure. Slidable clip 21 is preferably made of a radiopaque material to mark its location, and the location of the body cavity orifice, during radiographic viewing.

FIG. 2 shows details of an exemplary embodiment of the slidable clamp or clip 21. Illustrated is the preferred functional features of this clip: accessibility to and manipulability by the physician, minimal patient trauma, and a substantially circular shape. The slidable clip may be made of a polymeric, an elastomeric or a metallic material. Slidable clip 21 preferably has a means for closure that is readily operated with the physician's thumb and fingers, such as by engaging the tab(s) 21A, 21B. Slidable clip 21 also preferably adjusts and holds its position with members such as the meshing teeth 21C which are illustrated.

FIG. 3 shows a diagnostic catheter that incorporates a secondary or positioning balloon 30, which is considerably smaller than the primary balloon, as well as the slidable clip 21. Small or secondary balloon 30 may be made of polymeric materials suitable for medical device balloons, and preferably of an elastomeric material to enhance its holding effectiveness.

The distal portion of this catheter 10, including at least a portion of each of the primary balloon 20 and of the secondary balloon 30, is inserted into the patient's rectal cavity 40 in this embodiment. Slidable clip 21 has been positioned on the catheter for imparting the desired profile and size of the primary balloon 20 and so as to be located at the patient's orifice. In the preferred embodiment, the slidable clip 21 is radiopaque to mark its location during radiographic viewing. Large or primary balloon is inflated through hole 11, expanding the rectal cavity for radiation diagnosis. Secondary balloon 30 is inflated through holes 12 to secure the catheter assembly.

The proximal and distal ends of the secondary balloon 30 are adhered to the tube of the catheter 10, and the slidable clip 21 may be secured anywhere along the length of the secondary balloon (with the primary balloon usually being positioned therebetween). Secondary balloon 30 may be inflated either proximally or distally of the clip location, or, as shown in FIG. 3, both proximally and distally of the slidable clip 21.

Both the primary and secondary balloons are inflated by means of fluid communication through the small holes 11, 12. Each hole 11 communicates fluid from an isolated passage in the catheter 10 to the primary balloon 20. Hole(s) 12 communicate fluid from an isolated passage in the catheter body 23 to the secondary balloon 30 in this embodiment.

FIG. 4 illustrates a catheter for diagnosis in a bladder 41. The particular illustrated bladder 41 is a male bladder; however, the invention is suitable for use in female bladders as well. This diagnostic catheter includes a catheter tube or body 23A having a Foley-type catheter tube 23B with a detachable urine bag 23C. Also included are a primary balloon 20, a secondary balloon 30, and radiopaque reference line(s) 22. This diagnostic catheter is inserted through the urinary tract 42 into the bladder. A hole 19 at the distal tip of the body permits necessary urine flow during the procedure. Urine flows through hole 19 into a separate isolated communication line 17A (FIG. 5) in the catheter tube and into a branch 17 having the Foley-type catheter tube 23B.

As is the case for the FIG. 3 embodiment, the primary balloon 20 of this embodiment is inflated through one or more holes 11. Secondary balloon 30 is inflated through one or more holes 12. Both balloons are adhered to the catheter at their respective distal and proximal circumferential ends. The secondary balloon is located near the proximal end of the primary balloon. The distal end of the primary balloon is located just proximal of the distal tip of the catheter and includes the drainage hole 19. The illustrated primary balloon has radiopaque reference line(s) to provide a marking reference for the physician during radiographic viewing.

A branch 15 of the catheter tube 23A is at the proximal end of the fluid communication line for inflating the secondary balloon 30. A passageway 15A within the catheter tube 23A and branch 15 provides this fluid communication. The physician may attach any fitting, valve or regulator 16 to the branch which permits connection to and control of the source for inflation and deflation of the small balloon 30, such as the hypodermic syringe 24 shown in FIG. 1. Branch 32 is functionally similar to branch 15, except that it is used for isolated fluid communication with the primary balloon 20. A passageway 12A within the catheter tube 23A and branch 32 provides this fluid communication. Any fitting, valve or regulator 18 may be attached to this branch for connection to and control of the inflation and deflation fluid source for the large balloon. If desired, the same supply source, whether of biocompatible gas or liquid, through the use of isolated control means, can be used to inflate each balloon separately.

In the radiation diagnosis aspect of the invention, the physician selects the appropriate embodiment for the required diagnostic procedure, whether it includes one or more of the slidable clip and/or secondary balloon as an adjustable securement member, and/or a Foley-type catheter tube, and/or radiopaque reference line(s). The physician inserts the selected embodiment of the diagnostic catheter into and through the orifice of the body cavity to be diagnosed.

When the diagnostic catheter has a slidable clip, the physician inserts the desired amount of the primary balloon to the desired catheter penetration depth and then secures the clip at the body orifice by appropriate simplified manipulation of the clip. In those instances where a secondary balloon is included, the physician inflates this now by admitting the pressurized fluid through the appropriate branch at the proximal end of the catheter. When a Foley-type catheter is included, the drainage function of this device would operate as customary while the diagnosis is taking place with the primary balloon being inflated.

In the instance of a catheter as generally illustrated in FIG. 4, after initial insertion into the urinary tract, the physician inflates the small or secondary balloon to secure the assembly in place at the proximal end of the bladder. Next, the physician inflates the larger or primary balloon to thereby mark and/or manipulate the body cavity. When the radiopaque reference line(s) feature is included, the physician has a radiographic image of the boundary of the body cavity. If a radiographic inflating fluid is used to inflate the primary balloon, the physician also has a radiographic image of the internal walls of the body cavity when viewed in the usual manner of diagnosis. This allows the physician to see characteristics of the body cavity that will be of great assistance in diagnosing disease, such as potentially cancerous areas that can be treated by radiation therapy.

It will be understood that the embodiments of the present invention which have been described are illustrative of some of the applications and principles of the present invention. Various modifications may be made by those skilled in the art without departing from the true spirit and scope of the present invention.

I claim:

1. A radiation diagnostic catheter comprising: a flexible or semirigid tubular catheter body having primary longitudinal passageway therethrough; a marking balloon to insert biocompatible or radiopaque fluids to identify the position and shape of a body cavity of a living patient for radiation diagnosis, said balloon having a proximal end and a distal end, said balloon being positioned over a distal length of said tubular body; an opening between said longitudinal passageway of the tubular catheter body and said balloon by which a fluid is passed through said longitudinal passageway and into said marking balloon; and an adjustable securement assembly in engagement with said marking balloon for selectively defining said proximal end of the balloon at differing locations along said tubular catheter body; and said adjustable securement assembly includes a secondary balloon positioned inside of said marking balloon, said secondary balloon having an axial length which is substantially shorter than that of said marking balloon, said secondary balloon being secured at its proximal and distal ends to said tubular catheter body; further including a clip member engaging a proximal portion of the marking balloon at a location at which the marking balloon overlies the secondary balloon; and said clip member is sized and shaped to fit within an opening of the body cavity of the living patient, whereby selective movement of said clip member along the length of said secondary balloon varies the amount of the secondary balloon that inflates within the body cavity.

2. The diagnostic catheter in accordance with claim 1, wherein said clip member clamps over said marking balloon to prevent the fluid from flowing into and expanding the marking balloon at a location which is proximal of the clip.

3. The diagnostic catheter in accordance with claim 1, further including another opening in said tubular catheter body which communicates with another passageway isolated from said primary passageway through the tubular catheter body, whereby a fluid passes from a fluid source, through said another passageway and into said secondary balloon.

4. The diagnostic catheter in accordance with claim 1, wherein said distal end portion of the marking balloon extends distally beyond and is unsealed to said tubular catheter body.

5. The diagnostic catheter in accordance with claim 1, wherein a distal tip portion of said tubular catheter body extends distally out of and beyond said distal end portion of the marking balloon, and said distal end portion of the marking balloon is sealed to said tubular catheter body.

6. The diagnostic catheter in accordance with claim 5, further including a proximal portion of the tubular catheter body which remains external of the body cavity during use, and a distal opening in said distal tip portion of the tubular catheter body and a drainage passageway extending from said distal opening to said proximal portion of the tubular catheter body.

7. The diagnostic catheter in accordance with claim 1, further including a hypodermic syringe which is a reservoir for the biocompatible or radiopaque fluid, and said primary longitudinal passageway opens at its proximal end into said hypodermic syringe.

8. A radiation diagnosis catheter, comprising:

a primary balloon which provides marking of a body cavity through the use of radiopaque fluid and manipulation of the body cavity by expansive engagement between the balloon and the body cavity upon inflation of the balloon;

a catheter for insertion into the body cavity, said catheter has a first isolated fluid line and enables fluid communication between said first isolated fluid line and the interior of said primary balloon, said primary balloon being sealingly secured at least at its proximal end to a distal end portion of said catheter;

said catheter includes a hole opening into said primary balloon from said fluid line;

a supply of radiopaque fluid with which said fluid line communicates to deliver, control and evacuate radiopaque fluid into and out of said primary balloon;

said catheter and said primary balloon include respective distal ends, and said distal end of the primary balloon extends distally of said distal end of the catheter; and a slidable clip positioned over said proximal end of the primary balloon and slidable distally along said primary balloon, which slidable clip effectively seals off the primary balloon at a location proximal of the slidable clip when same is secured in place over the primary balloon.

9. A diagnostic catheter comprising:

a primary balloon which provides marking of a body cavity through the use of radiopaque fluid and manipulation of the body cavity by expansive engagement between the balloon and the body cavity upon inflation of the balloon;

a catheter for insertion into the body cavity, said catheter has a first isolated fluid line and enables fluid communication between said first isolated fluid line and the interior of said primary balloon, said primary balloon being sealingly secured least its proximal end to a distal end portion of said catheter;

said catheter includes a hole opening into said primary balloon from said fluid line;

a supply of radiopaque fluid with which said fluid line communicates to deliver, control and evacuate radiopaque fluid into and out of said primary balloon;

a slidable clip positioned over said proximal end of the primary balloon and slidable distally along said primary balloon, which slidable clip effectively seals off the primary balloon at a location proximal of the slidable clip when same is secured in place over the primary balloon; and said slidable clip includes a plurality of oppositely disposed intermeshing teeth to adjust the circumference of the slidable clip.

10. A diagnostic catheter comprising:

a primary balloon which provides marking of a body cavity through the use of radiopaque fluid and manipulation of the body cavity by expansive engagement between the balloon and the body cavity upon inflation of the balloon;

a catheter for insertion into the body cavity, said catheter has a first isolated fluid line and enables fluid communication between said first isolated fluid line and the interior of said primary balloon, said primary balloon being sealingly secured at least at its proximal end to a distal end portion of said catheter;

said catheter includes a hole opening into said primary balloon from said fluid line;

a supply of radiopaque fluid with which said fluid line communicates to deliver, control and evacuate radiopaque fluid into and out of said primary balloon;

a slidable clip positioned over said proximal end of the primary balloon and slidable distally along said primary balloon, which slidable clip effectively seals off the primary balloon at a location proximal of the slidable clip when same is secured in place over the primary balloon; and a secondary balloon located within said primary balloon and generally along a proximal length of said primary balloon, said slidable clip being slidable along the length of said secondary balloon, and said catheter includes another fluid line and hole opening into said secondary balloon for supplying pressurizable fluid thereinto.

11. A marking catheter in comprising:

an elongated tubular catheter body having a generally distally positioned port and a generally proximal portion, said catheter body having at least three longitudinal passageways therethrough, one of said passageways providing fluid-passing isolated communication between said generally distally positioned port and said generally proximal portion of the catheter body;

a large balloon secured at a proximal end thereof to said elongated tubular catheter body at a location proximal of a proximal-most one of said ports, said large balloon being secured at a distal end thereof to said elongated tubular catheter body at a location proximal of the distal-most one of said ports such that said distal-most port extends out of said large balloon and beyond its distal end, a central one of said ports opening into said large balloon for selectively inflating and deflating said large balloon;

a small balloon located near the proximal end of the large balloon, said small balloon being secured to the tubular catheter body at a location such that a proximal-most one of said ports opens into said Small balloon; and at least one radiopaque reference line is provided on the large balloon for radiopaque viewing.

12. A diagnostic catheter comprising:

a primary balloon which provides marking of a body cavity through the use of radiopaque fluid and manipulation of the body cavity by expansive engagement between the balloon and the body cavity upon inflation of the balloon;

a catheter for insertion into the body cavity, said catheter has a first isolated fluid line and enables fluid communication between said first isolated fluid line and the interior of said primary balloon, said primary balloon being sealingly secured at least at its proximal end to a distal end portion of said catheter;

said catheter includes a hole opening into said primary balloon from said fluid line;

a supply of radiopaque fluid with which said fluid line communicates to deliver, control and evacuate radiopaque fluid into and out of said primary balloon;

a slidable clip positioned over said proximal end of the primary balloon and slidable distally along said primary balloon, which slidable clip effectively seals off the primary balloon at a location proximal of the slidable clip when same is secured in place over the primary balloon; and said slidable clip is adjustable to vary the circumference of the slidable clip.

13. The diagnostic catheter in accordance with claim 12, wherein said slidable clip includes interfering members to adjust the circumference of the slidable clip.

14. A marking catheter comprising:

an elongated tubular catheter body having a generally distally positioned port and a generally proximal portion, said catheter body having at least three longitudinal passageways therethrough, each said passageway providing fluid-passing isolated communication between said generally distally positioned port and said generally proximal portion of the catheter body;

a large balloon secured at a proximal end thereof to said elongated tubular catheter body at a location proximal of a proximal-most one of said ports, said large balloon being secured at a distal end thereof to said elongated tubular catheter body at a location proximal of the distal-most one of said ports such that said distal-most port extends out of said large balloon and beyond its distal end, a central one of said ports opening into said large balloon for selectively inflating and deflating said large balloon;

a small balloon located near the proximal end of the large balloon, said small balloon being secured to the tubular catheter body at a location such that a proximal-most one of said ports opens into said small balloon; and radiopaque reference marking is provided on the large balloon for radiopaque viewing.

* * * * *

UNITED STATES PATENT AND TRADEMARK OFFICE
CERTIFICATE OF CORRECTION

PATENT NO. : 5,520,646
DATED     : May 28, 1996
INVENTOR(S) : Mark A. D'Andrea

It is certified that error appears in the above-indentified patent and that said Letters Patent is hereby corrected as shown below:

Col. 1, line 21, "use" should read --used--; line 53, insert a
    period --.-- after "like".
Col. 3, line 27, delete "typicality" and insert --typically--.
Col. 6, line 7, "having primary" should read --having a primary--.
Col. 7, line 37, "least its" should read --least at its--.
Col. 8, line 17, "catheter in comprising" should read --catheter
    comprising--; line 39, delete "Small" and insert --small--.

Signed and Sealed this

Fourth Day of March, 1997

Attest:

BRUCE LEHMAN

Attesting Officer      Commissioner of Patents and Trademarks